United States Patent
Chen et al.

(10) Patent No.: US 7,654,715 B1
(45) Date of Patent: Feb. 2, 2010

(54) SYSTEM AND METHOD FOR ILLUMINATING A SPECIMEN WITH UNIFORM ANGULAR AND SPATIAL DISTRIBUTION

(75) Inventors: Qibiao Chen, Fremont, CA (US); Charles N. Wang, Santa Clara, CA (US)

(73) Assignee: KLA-Tencor Technologies Corporation, Milpitas, CA (US)

( * ) Notice: Subject to any disclaimer, the term of this patent is extended or adjusted under 35 U.S.C. 154(b) by 152 days.

(21) Appl. No.: 11/836,216

(22) Filed: Aug. 9, 2007

(51) Int. Cl.
*F21V 33/00* (2006.01)

(52) U.S. Cl. .................. 362/552; 362/551; 362/268; 359/368

(58) Field of Classification Search .................. 362/551, 362/552, 253, 268; 359/368; 356/237.2–237.5
See application file for complete search history.

(56) References Cited

U.S. PATENT DOCUMENTS

| | | | | |
|---|---|---|---|---|
| 5,677,762 | A * | 10/1997 | Ortyn et al. | .................. 356/39 |
| 6,571,040 | B2 * | 5/2003 | Paris | .......................... 385/50 |
| 6,898,353 | B2 * | 5/2005 | Li | .............................. 385/43 |
| 6,969,177 | B2 * | 11/2005 | Li et al. | ......................... 362/19 |
| 7,001,055 | B1 | 2/2006 | Lange | |
| 7,304,731 | B2 * | 12/2007 | Hill | .......................... 356/237.2 |
| 2002/0122621 | A1 | 9/2002 | Li | |
| 2006/0268420 | A1 | 11/2006 | Cummings et al. | |
| 2007/0052953 | A1 | 3/2007 | Hill | |

* cited by examiner

*Primary Examiner*—Thomas M Sember
(74) *Attorney, Agent, or Firm*—Kevin L. Daffer; Daffer McDaniel, LLP

(57) ABSTRACT

A system for illuminating a specimen are disclosed herein. In general, the system may include an illumination source configured to generate light with an uneven distribution at a pupil plane and field stop of the system, a lightpipe coupled for redistributing the light across the pupil plane and field stop, and at least one optical element configured to direct the redistributed light onto a specimen. The lightpipe may generally include a cone-shaped portion and a rectangular-shaped portion. The cone-shaped portion is configured for modifying an angular distribution of the generated light, so that the redistributed light is uniformly distributed across the pupil plane of the system. The rectangular-shaped portion is formed contiguous with the cone-shaped portion and configured for modifying a spatial distribution of the generated light, so that the redistributed light is uniformly distributed across a field stop of the system. A method for illuminating a specimen and a system for inspecting a specimen are also disclosed herein.

22 Claims, 6 Drawing Sheets

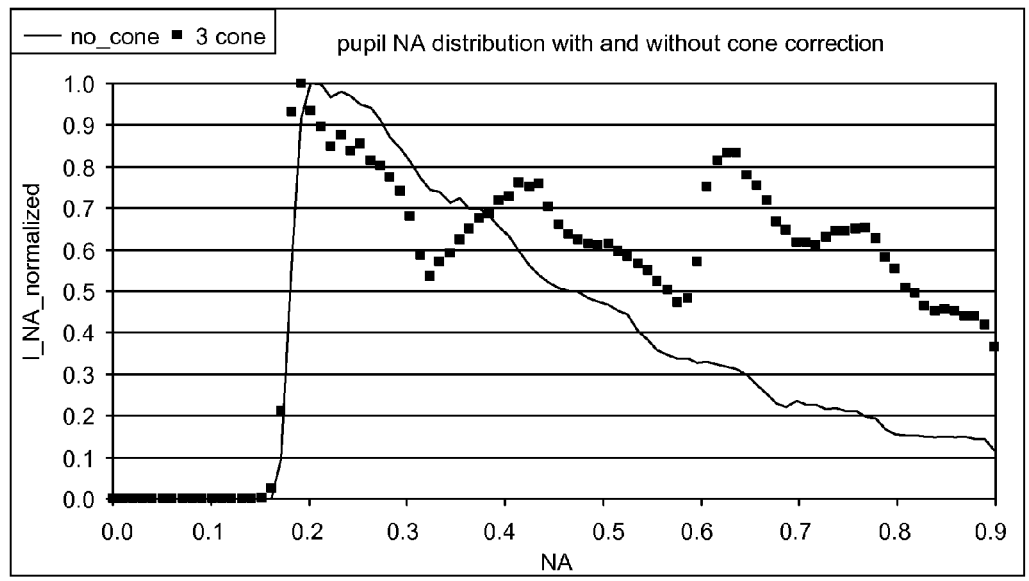
FIG. 7
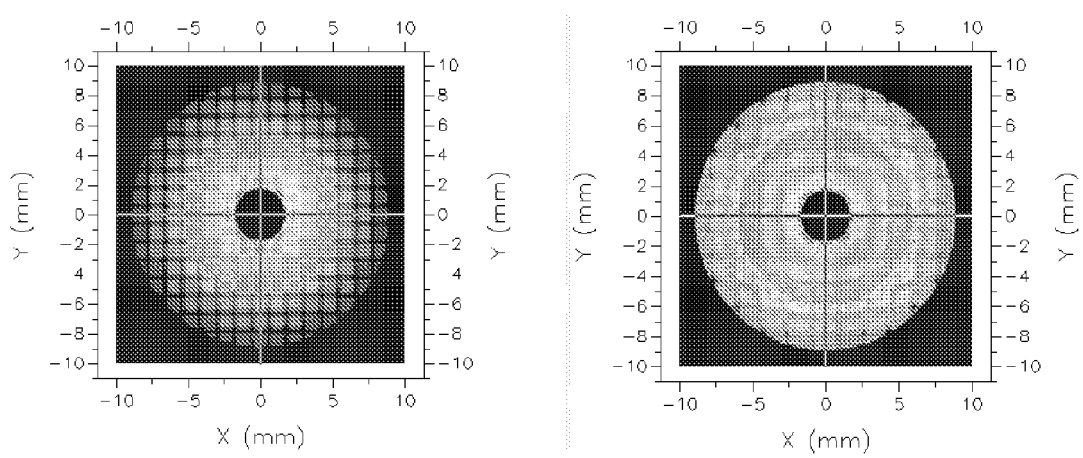
FIG. 8A  FIG. 8B

SYSTEM AND METHOD FOR ILLUMINATING A SPECIMEN WITH UNIFORM ANGULAR AND SPATIAL DISTRIBUTION

BACKGROUND OF THE INVENTION

1. Field of the Invention

This invention relates to illumination optics and, more particularly, to illumination pupil and field uniformity correction.

2. Description of the Related Art

The following descriptions and examples are given as background only.

Fabricating semiconductor devices such as logic and memory devices typically includes processing a substrate using a large number of semiconductor fabrication processes to form various features and multiple levels of the semiconductor devices. For example, lithography is a semiconductor fabrication process that involves transferring a pattern from a reticle to a resist arranged on a semiconductor wafer. Additional examples of semiconductor fabrication processes include, but are not limited to, chemical-mechanical polishing, etch, deposition, and ion implantation. Multiple semiconductor devices may be fabricated in an arrangement on a single semiconductor wafer and then separated into individual semiconductor devices.

Inspection processes are used at various steps during the manufacturing process to detect defects on wafers, promoting higher yield in the manufacturing process, and thus, higher profits. Inspection has always played an important role in the fabrication of semiconductor devices. However, the performance requirements of inspection systems has increased over the years, as a result of continually decreasing dimensions of the semiconductor devices. In particular, inspection systems require significantly higher resolution and sensitivity for detecting the small sized defects, which occur on advanced semiconductor wafers.

One factor affecting the resolution and sensitivity of the inspection system is the quality of light used to illuminate the specimen or semiconductor wafer. There are generally two types of light sources used within inspection systems. In some cases, a laser light source may be used to generate relatively bright light at relatively shorter wavelengths. However, laser light sources generate coherent light, which is undesirable for inspection for many reasons. For example, coherent light may produce speckle and/or ringing in the inspection images generated by the imaging sensor. Speckle decreases the resolution of the inspection system by decreasing the signal-to-noise ratio of the output signals generated by the system. Ringing introduces artifacts into the inspection images, which reduce sensitivity and make it difficult to detect defects. Although some illumination systems have been designed to reduce the speckle and ringing produced by coherent light sources, other systems avoid these problems altogether by illuminating the specimen with incoherent light.

An illumination system 100 comprising an incoherent light source is shown in FIG. 1. In an ideal case, the illumination system would produce a spatially uniform beam of light that covers the entire field of view (FOV) of the inspection system. The light generated by the illumination system would also have a uniform angular distribution over the entire numerical aperture (NA) transmission window of the inspection system. Any deviation from spatial or angular distribution uniformity will adversely affect the resolution and sensitivity of the inspection system, and therefore, is undesirable.

In the illustrated embodiment, illumination system 100 comprises a plasma arc lamp 110, an elliptical reflector 120, a homogenizer or lightpipe 150, and a pupil lens 160. The plasma arc lamp 110 may include any arc lamp which generates light in all directions and is suitable for inspecting a specimen. The elliptical reflector 120 is used to collect and reflect the light from arc lamp 110 to the entrance of homogenizer 150. The entrance of homogenizer 150 is located one focal length of the elliptical reflector away from the arc lamp.

In some cases, folding mirror 130 may be included so that some wavelengths of light (such as ultra-violet, UV, and deep ultra-violet, DUV wavelengths) are reflected to homogenizer 150, while other wavelengths (such as visible and infrared wavelengths) are transmitted through mirror 130 out of the optical path of the illumination system. Folding mirror 130 provides many advantages. For example, folding mirror reduces the system heat load, prolongs the lifetime of the illumination optics and reduces the noise background by removing unwanted visible and infrared light from the optical path. By folding the optical path (e.g., by 90°), folding mirror 130 reduces the system footprint and improves the rigidity and serviceability of the illumination system design.

Because the light generated by arc lamp 110 is typically not as bright as laser light, it is generally desirable that the elliptical reflector be configured to collect as much light as possible. The depth of the elliptical reflector is one factor that affects the intensity of the light generated at the illumination plane 140 of the illumination system. The reflector depth also affects the angular distribution of the generated light. For example, a deep ellipse may be used to provide greater intensity at the expense of a non-uniform angular distribution. On the other hand, a shallow ellipse may provide a substantially uniform angular distribution, but with less intensity.

FIG. 2 is included to illustrate the concept of reflector depth. As shown in FIG. 2, elliptical reflector 120 may be thought of as part of an ellipse. The ellipse has two focal points (foci_1 and foci_2). The arc lamp generates light in all directions at the first focal point (foci_1) of the ellipse. The light generated by arc lamp 110 is reflected from elliptical surface 120 over a 0°-360° azimuthal angle ($\phi$) and a 0°-180° polar angle ($\theta$) to the second focal point (foci_2) of the ellipse. The angular distribution of the reflected light depends on the angular magnification provided by the ellipse as the polar angle changes from 0°-180°. The angular magnification depends strongly on the depth of the ellipse, as described in more detail below.

As shown in FIG. 2, the ellipse may be generally described as having a semi-major axis (a), a semi-minor axis (b) and a distance (c) between the first focal point (foci_1) and the mid-point of the ellipse. A deep ellipse is produced when (a~c)>>b, or when the eccentricity of the ellipse is near 1. For example, the ellipse can be modeled by the equation:

$$a^2 = b^2 + c^2 \qquad \text{EQ. 1}$$

where c is defined as the distance between the first focal point (foci_1) and the mid-point of the ellipse. The eccentricity of the ellipse is, therefore, defined as:

$$e = c/a \qquad \text{EQ. 2}$$

When (a~c)>>b (i.e., in a deep ellipse), the distance (c) is approximately equal to the semi-major axis (a). This renders the eccentricity (e) of the deep ellipse substantially equal to 1.

The angular magnification of a deep ellipse varies significantly as the polar angle changes from 0°-180°. This produces a highly uneven angular distribution at the illumination plane 140 of the illumination system. On the other hand, the angular magnification of a shallow ellipse tends to be relatively constant across the polar angles. This produces a relatively uniform angular distribution of reflected light at the illumination plane. However, it is generally desirable to maximize the intensity of light generated by the illumination system to increase the detection resolution and sensitivity of the inspection system. As described in more detail below, many incoherent illumination systems use deep ellipses with relatively small widths to increase the intensity of light generated by the illumination system.

The intensity of light generated by the incoherent illumination system depends on the width (w), as well as the depth (d) of the elliptical reflector. In particular, the peak intensity of light supplied to the homogenizer entrance is a function of the eccentricity (e=c/a), which is close to 1 for a deep ellipse, and the amount of the light collected by the ellipse. The maximum collection angle or polar angle ($\theta$) determines the amount of light that can be collected by the reflector and is directly related to the depth (d) of the elliptical reflector and the width (w) of the reflector opening. In particular, the total amount of light collected by elliptical reflector 120 is determined by the ratio [d−(a−c)]/w. When combined with the eccentricity (e=c/a), the maximum collection angle determines the peak intensity/brightness of the light supplied to the homogenizer entrance. In order to increase resolution and sensitivity, it is important that this peak intensity be conserved at subsequent stages of the illumination system.

Homogenizer 150 is often used to improve the spatial uniformity of the light generated by the illumination system. A homogenizer or lightpipe is generally a solid glass rod or tubular passageway through which light rays can travel by total internal reflection. Homogenizers can have various cross-sectional shapes, such as rectangular (180, FIG. 3A), circular (190, FIG. 3B) or square (not shown). Rectangular and square homogenizers can also be formed by arranging four mirrors, so that the reflective surfaces of the mirrors create a rectangular or square passageway.

Rectangular homogenizers improve the spatial uniformity of the generated light by randomizing the light as it bounces through the homogenizer. Specifically, rectangular homogenizers are used to scramble the spatial distribution of the light, so that the light will be uniformly distributed at the field stop (not shown) of the illumination system. After passing through homogenizer 150, the light is directed by optical lens 160 to the pupil plane 170 of the illumination system. The optical lens 160 is generally located one focal length of the lens away from the exit of the homogenizer 150. The pupil plane 170 is generally located one focal length of the lens away from the optical lens 160.

Although homogenizer 150 improves the spatial uniformity of the light generated at the field stop, the light remains non-uniform with respect to angular distribution at the pupil plane 170 of the illumination system. In other words, rectangular homogenizers preserve the angles at which light bounces off the internal surfaces of the homogenizer. Rectangular homogenizers do not redistribute the angles at which light travels through the homogenizer, and therefore, do not change the angular distribution of the light produced at the pupil plane 170.

In some cases, an illumination system including a plasma arc lamp 110, a deep arc elliptical reflector 120 and a rectangular homogenizer 150 may produce a highly uneven angular distribution, with a majority of the light concentrated in the low angle or low numerical aperture (NA) range. In addition to reducing detection resolution and sensitivity, the highly concentrated low NA light generated by illumination system 100 may create problems for high NA bright-field (BF) and dark-field (DF) inspection systems. In particular, the highly concentrated low NA light may create light budget and lens damaging issues in such systems.

It is, therefore, desirable to provide an improved illumination system, which balances the energy distribution in the pupil plane, as well as the field stop of the illumination system. Preferably, the improved illumination system would be configured to redistribute an angular distribution of the light evenly over an entire numerical aperture (NA) transmission window of the inspection system with minimum light loss. In one embodiment, the improved illumination system may do so by providing a novel homogenizer designed to convert a majority of the low NA light to high NA light (or vice versa) at a specific location along the homogenizer.

SUMMARY OF THE INVENTION

The following description of various embodiments of systems and methods is not to be construed in any way as limiting the subject matter of the appended claims.

According to one embodiment, a system is provided herein for illuminating a specimen. In general, the system may include an illumination source configured to generate light with an uneven distribution at an illumination plane of the system, a lightpipe coupled for redistributing the light, and at least one optical element configured to direct the redistributed light onto a specimen. The illumination source may generally include a plasma arc lamp comprising a plasma source and an elliptical reflector. In one embodiment, the plasma source may be suitable for use in deep ultra-violet inspection systems. In such an embodiment, the plasma source may be selected from a group comprising Mercury (Hg) and Mercury Xenon (HgXe) sources. The elliptical reflector may include any elliptically-shaped reflective surface. In one embodiment, the elliptical reflector may comprise a relatively deep ellipse (having, e.g., an eccentricity close to 1) and a relatively large maximum collection angle. This may enable the elliptical reflector to collect as much light as possible from the plasma source (i.e., maximize the intensity of the collected light).

In general, the lightpipe comprises a cone-shaped portion and a rectangular-shaped portion. The cone-shaped portion is configured for modifying an angular distribution of the generated light, so that the redistributed light is uniformly distributed across a pupil plane of the system. The rectangular-shaped portion is configured for modifying a spatial distribution of the generated light, so that the redistributed light is uniformly distributed across a field stop of the system. Unlike conventional lightpipes, the rectangular-shaped portion is formed contiguous with the cone-shaped portion. In one embodiment, the rectangular and cone-shaped portions are fabricated separately and bonded together at opposing ends. Substantially any materials and/or methods may be used to bond the two portions together, as long as the bond creates an optically seamless and rugged transition between the rectangular and cone-shaped portions.

In general, the cone-shaped portion may include a first cone, whose cross-sectional area increases along a length of the first cone, and a second cone whose cross-sectional area decreases along a length of the second cone. In one embodiment, the first cone is formed contiguous with the second cone. In another embodiment, the cone-shaped portion includes a third cone formed between and contiguous with the first and second cones. In some cases, the third cone may have a substantially uniform cross-section along an entire length of the third cone. In other cases, the cross-sectional area of the third cone may decrease along a length of the third cone.

More specifically, the first cone may be described as having a positive taper angle, wherein the third cone may be described as having a substantially zero taper angle, and wherein the second cone may be described as having a negative taper angle. The taper angles of the three cones are individually selected to convert or preserve the numerical aperture distribution of light entering the cone-shaped portion. For example, the light generated by the illumination source enters the cone-shaped portion with low, medium and high numerical apertures (NA).

In one embodiment, the first cone may have a positive taper angle for converting light that enters the cone-shaped portion with high NA into lower NA. The third cone may have a substantially zero taper angle for preserving light that enters the cone-shaped portion with medium NA. The second cone may have a negative taper angle for converting light that enters the cone-shaped portion with low NA, as well as light converted to low NA by the positive taper angle, into higher NA. In particular, the negative taper angle may be adapted to increase the numerical aperture of substantially all light that enters the cone-shaped portion by ΔNA.

According to one embodiment, a system is provided herein for inspecting a specimen. In general, the system may include an illumination source comprising a plasma source and an elliptical reflector, a lightpipe coupled for receiving an uneven distribution of light from the illumination source, at least one optical element configured to direct light which has been redistributed by the lightpipe onto a surface of the specimen, and a detection subsystem configured to generate output signals in response to light propagating from the surface of the specimen. The output signals generated by the detection system may be used to inspect the specimen.

The lightpipe may be configured as described above. For example, the lightpipe may include a rectangular-shaped portion for modifying a spatial distribution of the light generated by the illumination source, so that the redistributed light is uniformly distributed across a field stop of the illumination system and a field plane within the field of view (FOV) of the inspection system. In addition, the lightpipe may include a cone-shaped portion for modifying an angular distribution of the light generated by the illumination source, so that the redistributed light is uniformly distributed across a pupil plane of the system. The rectangular-shaped and cone-shaped portions may be configured as described herein. The cone-shaped portion may be configured to redistribute the light evenly over an entire numerical aperture (NA) transmission window of the inspection system without significant light loss. In one embodiment, the lightpipe may provide a light loss of less than about 20%. In another embodiment, the lightpipe may provide a light loss of about 10-15%.

According to another embodiment, a method is provided herein for illuminating a specimen. In general, the method may include generating light having an uneven angular and spatial distribution, directing the light to a single lightpipe configured to redistribute the angular and spatial distribution of the light in a uniform manner, and transmitting the redistributed light onto the specimen. As noted above, the light may be generated by a plasma source and collected by a deep elliptical reflector (e.g., having an eccentricity close to 1). The single lightpipe may include a cone-shaped portion configured to redistribute the angular distribution of the light and a rectangular-shaped portion, which is formed contiguous with the cone-shaped portion and configured to redistribute the spatial distribution of the light.

BRIEF DESCRIPTION OF THE DRAWINGS

Other objects and advantages of the invention will become apparent upon reading the following detailed description and upon reference to the accompanying drawings in which:

FIG. 7 is a graph illustrating exemplary NA distributions at a pupil plane of the system shown in FIG. 5 with and without the improved homogenizer shown in FIGS. 6A-6C;

FIG. 8A is a simulated pupil image at the pupil plane of a bright-field inspection system without the improved homogenizer shown in FIGS. 6A-6C;

FIG. 8B is a simulated pupil image at the pupil plane of a bright-field inspection system including the improved homogenizer shown in FIGS. 6A-6C.

Figure 1:
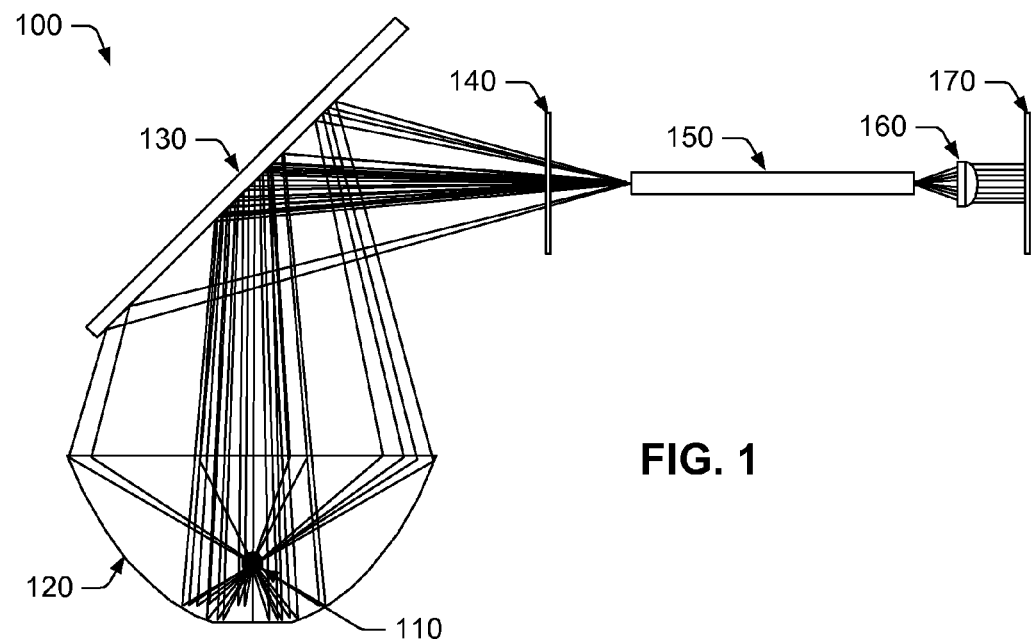
FIG. 1 is a schematic diagram illustrating a side view of a system configured to illuminate a specimen with incoherent light.

While the invention is susceptible to various modifications and alternative forms, specific embodiments thereof are shown by way of example in the drawings and will herein be described in detail. It should be understood, however, that the drawings and detailed description thereto are not intended to limit the invention to the particular form disclosed, but on the contrary, the intention is to cover all modifications, equivalents and alternatives falling within the spirit and scope of the present invention as defined by the appended claims.

DETAILED DESCRIPTION OF PREFERRED EMBODIMENTS

As used herein, the term specimen refers to a reticle or a wafer. The terms reticle and mask are used interchangeably herein. A reticle generally includes a transparent substrate such as glass, borosilicate glass, and fused silica having opaque regions formed thereon in a pattern. The opaque regions may be replaced by regions etched into the transparent substrate. Many different types of reticles are known in the art, and the term reticle as used herein is intended to encompass all types of reticles.

As used herein, the term wafer generally refers to substrates formed of a semiconductor or non-semiconductor material. Examples of such a semiconductor or non-semiconductor material include, but are not limited to, monocrystalline silicon, gallium arsenide, and indium phosphide. Such substrates may be commonly found and/or processed in semiconductor fabrication facilities.

A wafer may include one or more layers formed upon a substrate. For example, such layers may include, but are not limited to, a resist, a dielectric material, a conductive material, and a semiconductive material. Many different types of such layers are known in the art, and the term wafer as used herein is intended to encompass a wafer including all types of such layers.

One or more layers formed on a wafer may be patterned or unpatterned. For example, a wafer may include a plurality of dies, each having repeatable patterned features or periodic structures. Formation and processing of such layers of material may ultimately result in completed devices. Many different types of devices may be formed on a wafer, and the term wafer as used herein is intended to encompass a wafer on which any type of device known in the art is being fabricated.

Turning now to the drawings, it is noted that the figures are not drawn to scale. In particular, the scale of some of the elements of the figures is greatly exaggerated to emphasize characteristics of the elements. It is also noted that the figures are not drawn to the same scale. Elements shown in more than one figure that may be similarly configured have been indicated using the same reference numerals.

The resolution and sensitivity of an inspection system depends, at least in part, on the quality of light used to illuminate a specimen under inspection. In incoherent systems, the detection resolution and sensitivity depends on the spatial distribution of illumination light at the field stop, as well as the angular distribution of illumination light at the pupil plane of the illumination system. An illumination system is said to provide spatial uniformity when a substantially equal density of light rays exists throughout the plane of the field stop within the field of view (FOV) of the inspection system. An illumination system is said to provide angular uniformity when incident angles of the light rays at the pupil plane are uniformly distributed across a numerical aperture (NA) transmission window of the inspection system. An illumination system providing both spatial and angular uniformity may increase resolution and sensitivity of the inspection system by providing illumination, which covers the entire field of view (FOV) and NA transmission window of the inspection system. However, the detection resolution and sensitivity is also dependent on the intensity of light generated by the illumination system. As described in more detail below, significant light loss within the illumination system reduces the intensity of light supplied to the specimen, thereby reducing detection resolution and sensitivity.

Figure 4:
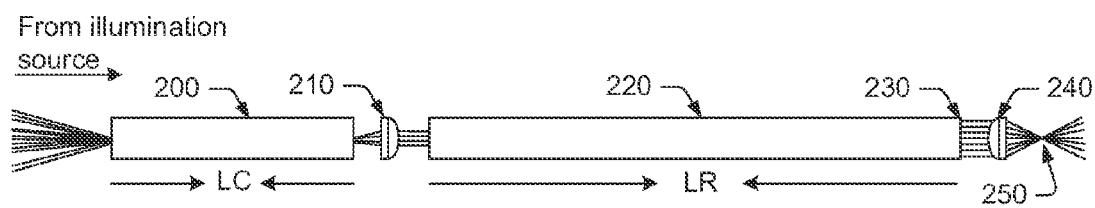
FIG. 4 is a schematic diagram illustrating a side view of a circular homogenizer combined with a rectangular homogenizer via intervening optical components.

An illumination system and method for uniformly illuminating a pupil plane and field stop of an inspection system is described in commonly assigned U.S. Pat. No. 7,001,055 to Lange, which is incorporated herein by reference. In this patent, Lange describes how a circular lightpipe may be combined with a rectangular lightpipe to modify the angular and spatial distribution of light generated by an incoherent light source. More specifically, Lange describes how a circular lightpipe (200, FIG. 4) may be arranged in the optical path of the illumination system for receiving light from a plasma arc lamp (not shown) and elliptical reflector (not shown). As light travels through the circular lightpipe 200, the light reflects off the cylindrical inner surface of the lightpipe, so that the light is spatially redistributed at the exit of the lightpipe and the field stop 250 of the illumination system.

The light exiting circular lightpipe 200 is directed by lens 210 to rectangular lightpipe 220. Lens 210 is arranged one focal length of lens 210 away from circular lightpipe 200 and rectangular lightpipe 220. As the light passes through rectangular lightpipe 220, the light totally internally reflects off the rectangular shaped inner surface, so that the distribution of light is spatially uniform at the exit of lightpipe 220, which is located at the pupil plane 230 of the illumination system. Lens 240 directs the light exiting rectangular lightpipe 220 through field stop 250. Additional optics are used to image the pupil plane 230 onto the objective lens pupil (not shown) of the inspection system (not shown).

Although each lightpipe (200, 220) functions to redistribute the light spatially, Lange notes that combining the lightpipes in the above manner produces light, which is both uniformly distributed in the angular and spatial respects at the pupil plane 230 and field stop 250 of the illumination system. In particular, Lange notes that circular lightpipe 200 acts as a field stop randomizer by randomizing the light rays across field stop 250, while rectangular lightpipe 220 acts as a pupil randomizer by randomizing the light rays across pupil 230.

However, the illumination system disclosed by Lange may not be useful in all inspection systems. First of all, the circular and rectangular lightpipes function to randomize the light rays by repeatedly reflecting or bouncing the light rays off the internal surfaces of the lightpipes. This randomization provides little to no control over the final light distribution. The lightpipes disclosed by Lange are, therefore, unsuitable for use in systems that are specifically concerned with converting a predominantly low NA distribution to a predominantly high NA distribution (or vice versa). The lightpipes disclosed by Lange also produce significant light loss (e.g., up to 64%), which decreases the intensity of light supplied to the specimen, ultimately degrading the detection resolution and sensitivity of the inspection system.

Another disadvantage of the Lange patent is that the combined lightpipes have a relatively long total length (e.g., about 650 mm to about 1150), which may make it difficult, if not impossible, to retro-fit the combined lightpipes into existing illumination systems. The length of the combined lightpipes also increases the amount of light attenuated or lost through the lightpipe. For example, attenuation through the lightpipe may be approximately equal to:

$$\text{Loss} \sim \exp^{-\alpha L} \qquad \text{EQ. 3}$$

where $\alpha$ is the absorption coefficient and L is the length of the lightpipe. As seen in EQ. 3, the amount of light transmitted through the lightpipe may approach zero as the length (L) of the lightpipe and/or the absorption coefficient ($\alpha$) of the lightpipe material increases. Light loss is especially problematic in DUV inspection systems, since the amount of DUV light generated by the plasma arc is typically very weak and the absorption coefficient ($\alpha$) of the lightpipe material increases as the wavelength of generated light decreases into the DUV region. In addition, the lightpipes are separated by an intervening lens 210, which increases the complexity of the illumination system, decreases transmission efficiency and increases transmission loss. The intervening lens also reduces system stability, increases alignment difficulties and makes the system more costly to make and maintain.

Figure 5:
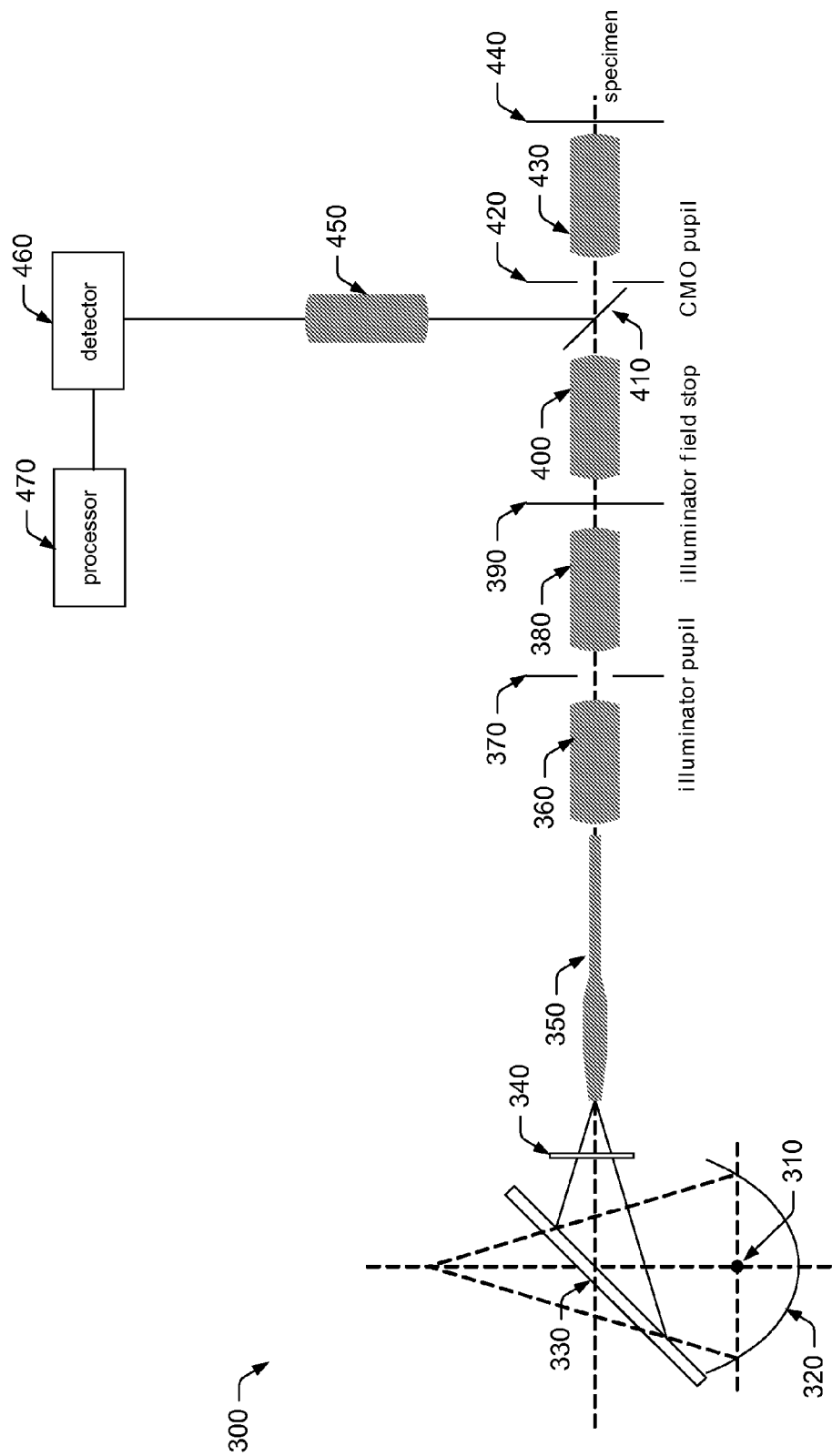
FIG. 5 is a schematic diagram illustrating a side view of a system configured to inspect a specimen, according to one embodiment.
Figure 6A:
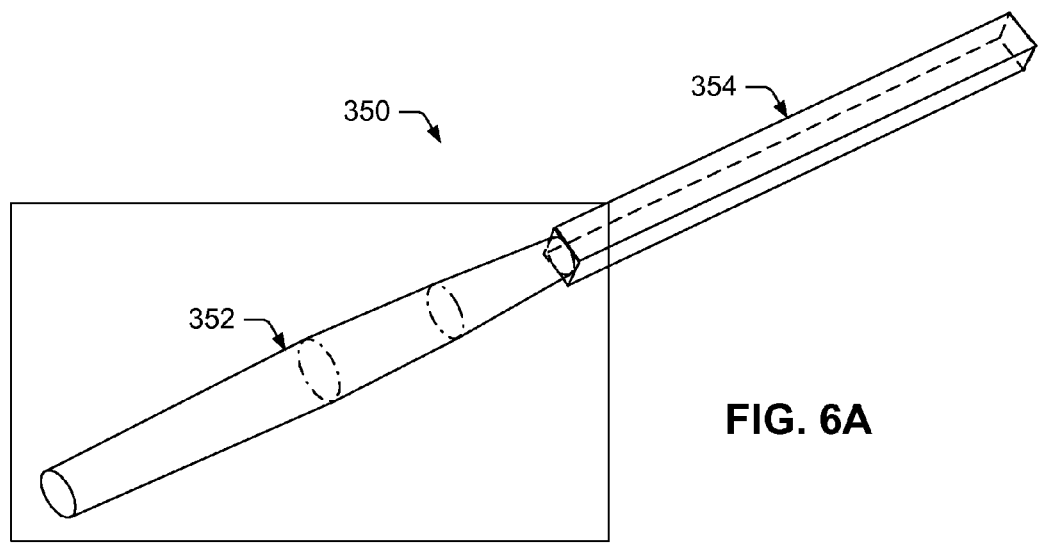
FIG. 6A is a three-dimensional diagram illustrating an improved homogenizer, according to one embodiment.
Figure 6B:
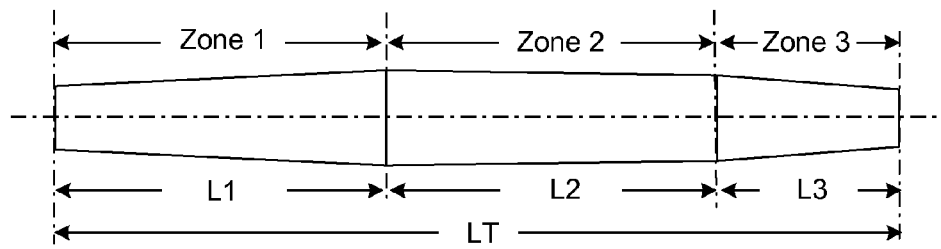
FIG. 6B is a schematic diagram illustrating a side view of a cone-shaped portion of the improved homogenizer, according to one embodiment.
Figure 6C:
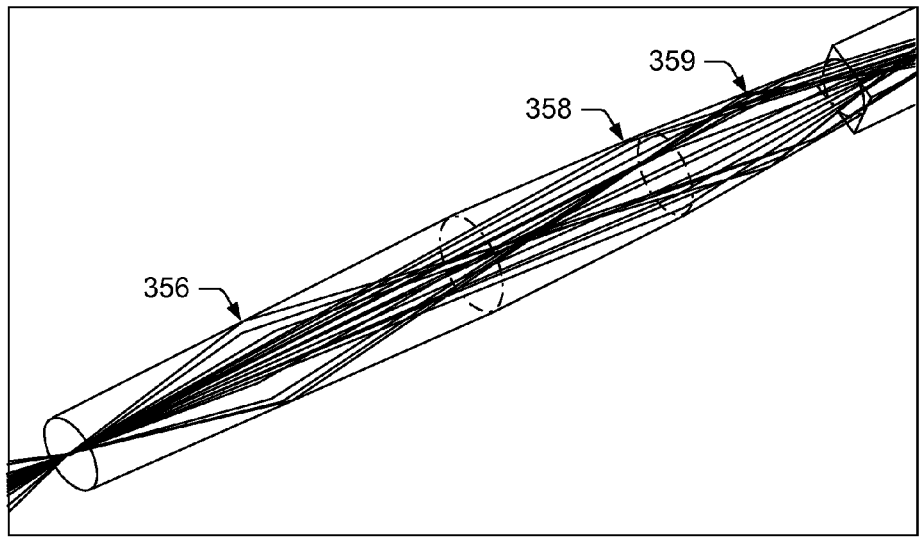
FIG. 6C is a three-dimensional diagram illustrating exemplary light travel through the cone-shaped portion of the improved homogenizer, according to one embodiment.
Figure 9:
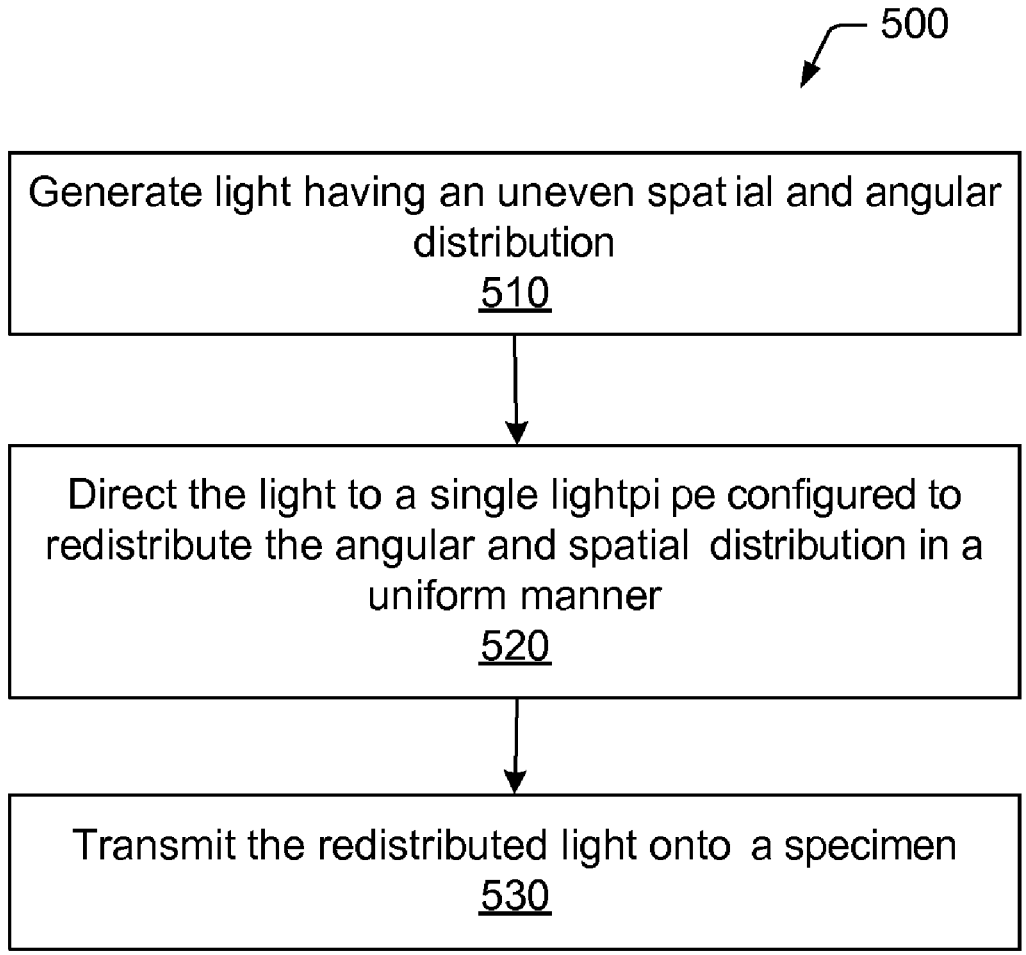
FIG. 9 is a flowchart diagram of a method for illuminating a specimen, according to one embodiment.

An improved illumination system and method for uniformly illuminating a pupil plane and field stop of an inspection system are shown in FIGS. 5, 6, and 9. In particular, FIG. 5 illustrates one embodiment of a system configured to inspect a specimen using light from an incoherent illumination system. FIGS. 6A-C illustrates one embodiment of a lightpipe, which may be used within an incoherent illumination system to provide both spatial and angular distribution uniformity. FIGS. 7-8 illustrate exemplary results of the angular correction provided by the lightpipe. FIG. 9 illustrates one embodiment of a method for illuminating a specimen.

As shown in FIG. 5, inspection system 300 may generally include an illumination system, imaging optics and a detection system. In one embodiment, the illumination system may be similar to the one shown in FIG. 1. For example, the illumination system may generally include a plasma arc lamp 310, an elliptical reflector 320 and a lightpipe 350. In one embodiment, plasma arc lamp 310 may include a plasma source, which is suitable for use in a deep ultra-violet (DUV) inspection system, such as a Mercury (Hg) or Mercury Xenon (HgXe) source. However, plasma arc lamp 310 is not limited to the sources explicitly mentioned herein and may comprise substantially any incoherent light source, which generates light in all directions and is suitable for use in an inspection system.

The elliptical reflector 320 is used to collect and reflect light from plasma arc lamp 310 to the entrance of lightpipe 350. The plasma arc lamp 310 is located at the first focal point (foci_1) of the elliptical reflector. The entrance of lightpipe 350 is located at the second focal point (foci_2) of the elliptical reflector. In the illustrated embodiment, folding mirror 330 is included so that some wavelengths of light (such as ultra-violet, UV, and deep ultra-violet, DUV wavelengths) are reflected to lightpipe 350, while other wavelengths (such as visible and infrared wavelengths) are transmitted through mirror 330 out of the optical path of the illumination system. Folding mirror 130 provides many advantages including, but not limited to, reducing the system heat load, prolonging the lifetime of the illumination optics, reducing the noise background, reducing the system footprint and improving the rigidity and serviceability of the illumination system design. In some cases, folding mirror 330 may enable additional functionality by allowing other optical components to be combined with the elliptical reflector to control/monitor the generated light. However, folding mirror 330 may not be included in all embodiments of the invention. If folding mirror 330 is eliminated, plasma arc lamp 310, elliptical reflector 320 and lightpipe 350 may be arranged on the same optical axis.

One or more illuminator relay optics may be used to collect the light exiting lightpipe 350 and direct the light to the field plane or wafer plane, which is conjugate to the sensor plane and the illuminator field stop plane. In one embodiment, the one or more illuminator relay optics may include illuminator pupil lens 360, field lens 380 and system pupil lens 400, as shown in FIG. 5. Lenses 360, 380, and 400 may include any appropriate refractive lens or reflective lens known in the art. Lenses 360, 380, and 400 may also include more than one lens, in some embodiments.

In one embodiment, lenses 360, 380, and 400 may be located at fixed positions within the illumination system. For example, the illuminator pupil lens 360 may be located one focal length of lens 360 away from the exit of lightpipe 350 and one focal length of lens 360 away from the pupil plane 370 of the illumination system. Field lens 380 may be located one focal length of lens 380 away from the pupil plane 370 and one focal length of lens 380 away from the field stop 390 of the illumination system. System pupil lens 400 may be located one focal length of lens 400 away from field stop 390 of the illumination system and one focal length of lens 400 away from the pupil plane 420 of the inspection system. In this manner, light exiting lightpipe 350 is collimated and directed to the pupil plane 370 of the illumination system by pupil lens 360. Field lens 380 collimates and focuses the light from the pupil plane 370 to the field stop 390 of the illumination system. The system pupil lens 400 then refocuses the light collimated by the field lens 380 to the pupil plane 420 of the inspection system.

In some cases, the illumination system described above may generate an uneven distribution of light at the pupil plane 370 and field stop 390 of the illumination system. In some cases, the generated light may comprise an uneven spatial distribution at the illumination plane 340, due to the manner in which the light is generated by the plasma arc lamp and reflected to the lightpipe entrance by the elliptical reflector. The generated light may also be uneven with respect to angular distribution at the illumination plane. In some cases, the uneven angular distribution may be a result of the uneven angular magnification provided by elliptical reflector 320. For example, the light from plasma arc lamp 310 is reflected from elliptical surface 320 over a 0°-360° azimuthal angle (φ) and a 0°-180° polar angle (θ) to the second focal point (foci_2) of the elliptical reflector. However, the light reflected from the elliptical surface is magnified differently as the polar angle changes from 0°-180°. As noted above, deeper ellipses tend to provide a highly variable amount of angular magnification across the polar angles, while shallower ellipses provide more consistency.

Figure 2:
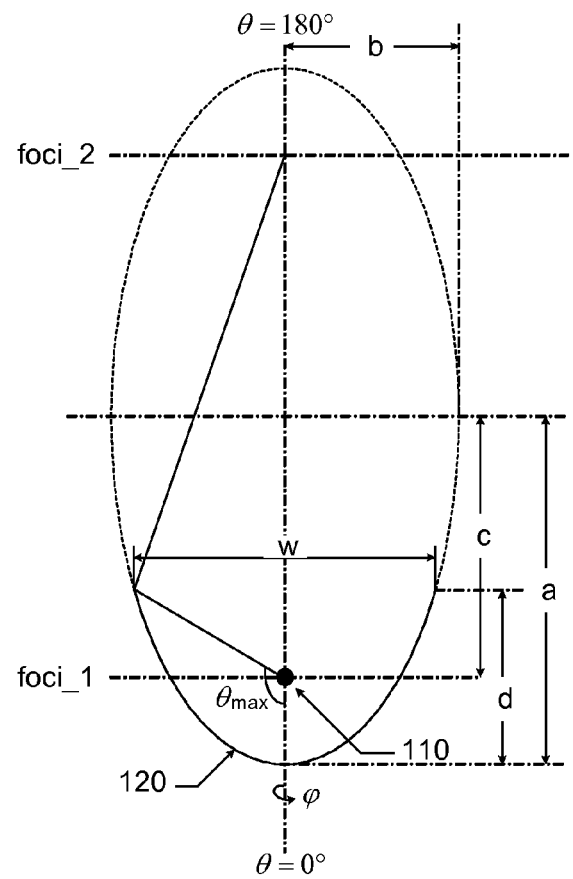
FIG. 2 is a mathematical diagram illustrating various characteristics of an elliptical reflector.
Figure 3A:
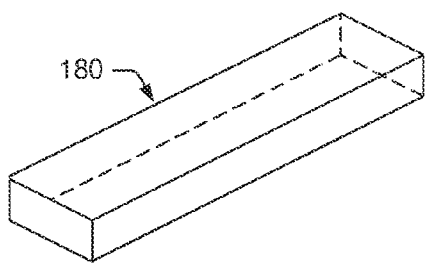
FIG. 3A is a three-dimensional diagram illustrating a homogenizer with a rectangular cross-section.
Figure 3B:
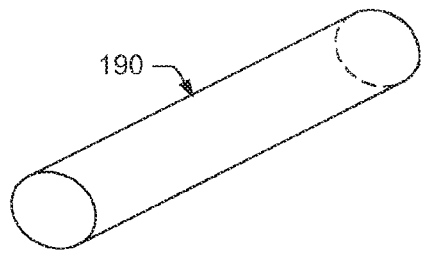
FIG. 3B is a three-dimensional diagram illustrating a homogenizer with a circular cross-section.

In at least one embodiment, elliptical reflector 320 includes a relatively deep ellipse with a relatively narrow width, so as to maximize the intensity of light generated by the illumination system. As noted above, a deep ellipse is produced when the semi-major axis (a) is much longer than the semi-minor axis (b) of the ellipse. A deep ellipse may also be described as having an eccentricity close to 1, where the eccentricity (e) is defined as c/a, and where c is defined as the distance between the first focal point (foci_1) and the mid-point of the ellipse (see, FIG. 2).

Although a deep ellipse with a narrow width (and, therefore, large maximum collection angle) maximizes the amount of light collected from plasma arc lamp 310, the deep ellipse produces a highly uneven angular distribution of light at the pupil plane 370 of the illumination system. This may create problems for some inspection systems. In some cases, for example, the light rays generated at pupil plane 370 may be predominantly low NA (e.g., about [0.18, 0.5]). However, most bright-field (BF) and dark-field (DF) inspection systems are predominantly high NA systems (e.g., systems with a max NA of about 0.9). Supplying low NA light to high NA inspection systems creates many problems including, but not limited to, reduced detection resolution and sensitivity, light budget issues and lens damaging issues.

For example, if the pupil intensity distribution comprises mainly low NA illumination, the total light power would need to be increased to meet the high NA light budget for high NA inspection systems. In most cases, there is simply not enough high NA light to meet the light budget or signal/noise requirements of a high NA inspection system with the desired resolution. Even if it were possible to provide enough total light power, the total amount of unused light power will increase significantly at least up to the illuminator pupil plane. This significantly increases the power density of light supplied to the relay optics. In some cases, the power density may reach damaging thresholds pre-maturely, thereby reducing the life time of the illumination subsystem.

Lightpipe 350 is used to redistribute the light generated by the illumination system described above. However, lightpipe 350 differs from conventional lightpipes in many ways. First of all, lightpipe 350 uses a single lightpipe to provide both spatial and angular uniformity of the illumination light. The single lightpipe is shown in FIG. 6A and generally described as including a cone-shaped portion 352 and a rectangular-shaped portion 354.

Unlike conventional lightpipes, which separate two lightpipes with intervening optics, the rectangular-shaped portion 354 is formed contiguous with the cone-shaped portion 352. In one embodiment, the two portions of the lightpipe may be fabricated from a continuous piece of material. The lightpipe material may be selected from a variety of optically transmissive materials including, but not limited to, glass, acrylic, fused silica, plastic and quartz. Different materials may be selected for transmitting light in different transmission bands. In one embodiment, fused silica may be selected to transmit light in the DUV range.

In other embodiments, the two portions of the lightpipe may be fabricated separately and bonded together at opposing ends to simply the manufacturing process. In one embodiment, the exit surface of the cone-shaped portion 352 may be bonded to the entrance surface of the rectangular-shaped portion 354. The opposite may be true in alternative embodiments of the invention. In one embodiment, the opposing ends of the lightpipes may be bonded together with an optical grade epoxy. In other embodiments, a bonding process that provides true optical contact without epoxy may be highly desired. In DUV applications, for example, epoxy may not be used to avoid absorption related damaging issues. In these applications, the bonding surfaces of the two portions may be fused together at atomic level. It is noted, however, that substantially any other bonding material and/or method may be used, which provides an optically seamless and rugged transition between the two portions.

The rectangular-shaped portion is generally configured for modifying the spatial distribution of the generated light, so that the redistributed light is uniformly distributed across the field stop 390 of the illumination system. The cone-shaped portion is generally configured for modifying the angular distribution of the generated light, so that the redistributed light is uniformly distributed across the pupil plane 370 of the illumination system. Unlike conventional lightpipes, which attempt to provide angular uniformity by randomizing light rays as they travel down the length of the lightpipe, the cone-shaped portion shown in FIGS. 6A-C is specifically designed to convert one numerical aperture (NA) range into another. In some embodiments, for example, the cone-shaped portion 352 may be configured to convert the predominantly low NA distribution from deep elliptical reflector 320 into a predominantly high NA distribution at the pupil plane 370. However, cone-shaped portion 352 is not limited to converting low NA distributions to high NA distributions in all embodiments of the invention. In some embodiments, the cone-shaped portion may be modified to produce substantially any angular distribution of light at the pupil plane.

Another distinction between cone-shaped portion 352 and conventional lightpipes is that cone-shaped portion 352 includes a substantially non-uniform cross-sectional area. In general, the cone-shaped portion may include a first cone whose cross-sectional area increases along a length of the first cone, and a second cone whose cross-sectional area decreases along a length of the second cone. In one embodiment, the two cones (or zones as they are alternately described) may be specifically configured to convert the predominantly low NA distribution provided by the incoherent illumination system described above into a high NA distribution suitable for use in a BF or DF inspection system. For example, the second cone may include a negative taper angle for increasing the numerical aperture (NA) of substantially all light that enters the cone-shaped portion by $\Delta NA$. In order to minimize light loss beyond the system NA transmission window, the first cone may be implemented with a positive taper angle, so that light entering the cone-shaped portion with high NA is first converted into lower NA before it is subsequently increased by $\Delta NA$.

In one embodiment (not shown), the first cone may be formed contiguous with the second cone. For example, a lathe-type machine may be used to rotate a glass rod (or other lightpipe material) while the outer surface of the glass rod is ground down to produce a desired shape of the cone-shaped portion. Once the final shape is obtained, the outer surface of the cone-shaped portion may be polished to improved surface quality. However, it is important that the first cone transitions smoothly into the second cone. In particular, the reflective surfaces of the first and second cones should form a continuous curve to minimize loss within the lightpipe. In some cases, more than two cones or zones may be stacked together to form a continuous curve. FIGS. 6A-C illustrates one embodiment in which three cones are stacked together to form a cone-shaped portion 352 with a continuous curve. It is noted, however, that the cone-shaped portion is not limited to the specific embodiments described herein. In a general embodiment, any number of cones or zones may be stacked together, as long as the reflective surfaces of the cones form a smooth, continuous curve.

FIG. 6B illustrates one preferred embodiment of a cone-shaped portion 352 in accordance with the invention. In the illustrated embodiment, cone-shaped portion 352 includes a first cone (Zone 1) of increasing cross-sectional area, a second cone (Zone 2) of substantially constant cross-sectional area and a third cone (Zone 3) of decreasing cross-sectional area. As described in more detail below, the three cones or zones of cone-shaped portion 352 may be configured to convert the predominantly low NA distribution provided by the incoherent illumination system described above into a high NA distribution suitable for use in a BF or DF inspection system. However, one skilled in the art would understand how the cone-shaped portion could be modified, in alternative embodiments of the invention, to redistribute the light in accordance with substantially any angular distribution.

FIG. 6C illustrates one manner in which light generated by the illumination system may enter the cone-shaped portion. In general, illumination light may enter the cone-shaped portion with low, medium and high numerical apertures (NA). If the lightpipe 350 is used within the illumination system described above, a majority of the illumination light may be concentrated in the low NA range. Remaining portions of the illumination light may enter the cone with medium to high NA. Although each of the cones is configured to modify the angular distribution of the illumination light, the three cones are individually configured for addressing a substantially different NA range. For example, the first cone (Zone 1) may have a positive taper angle for converting light that enters the cone-shaped portion with high NA into lower NA. The second cone (Zone 2) may have a substantially zero taper angle for preserving light that enters the cone-shaped portion with medium NA. The third cone (Zone 3) may have a negative taper angle for increasing the numerical aperture (NA) of substantially all light that enters the cone-shaped portion by $\Delta NA$.

As used herein, the taper angle is defined as the angle which is created at the entrance of each cone, between the outer surface of the cone and an axis parallel to the length of the cone. A positive taper angle is created when the cross-sectional area of the cone increases along a length of the cone. A negative taper angle is created when the cross-sectional area of the cone decreases along a length of the cone. A substantially zero taper angle is created when the cross-sectional area of the cone is substantially uniform along the length of the cone.

The positive taper angle of the first cone converts high NA light into lower NA light. The positive taper angle also enables the high NA light to strike the reflective surface of the cone-shaped portion farther away from the entrance of the first cone. In particular, the positive taper angle enables the high NA light to strike the reflective surface at a location 356, which causes the light to be internally reflected to a location 359 within the third cone. The high NA light is converted into lower NA light at the first bounce (i.e., at location 356), and increased by ΔNA when the light strikes the reflective surface of the third cone at the second bounce (i.e., at location 359). Providing the first cone with a positive taper angle ensures that the high NA light will reflect or bounce off the reflective surface of the cone-shaped portion no more than twice. This restriction enables the cone-shaped portion to redistribute the light evenly over a NA transmission window of the inspection system with minimum light loss.

For example, if the first cone were modified to include a substantially uniform cross-section, the high NA light entering the cone-shaped portion would bounce off the reflective surface many times before the light entered the third cone, possibly converting the light back to high NA after it was converted into lower NA at the first bounce. The high NA light entering the third cone would be increased in the third cone by ΔNA, as described in more detail below. In some cases, increasing the high NA light by ΔNA may cause significant light loss by pushing a portion of the redistributed light outside of the NA transmission window of the inspection system. This light loss is avoided by configuring the first cone with a positive taper angle.

In one embodiment, the substantially zero taper angle of the second cone may preserve the angular distribution of the light that enters the cone-shaped portion with medium NA. For example, the substantially uniform cross-section of the second cone may enable light with medium NA to bounce off the reflective surface of the second cone (at location 358) at substantially the same angle at which the light entered the cone-shaped portion. The medium NA light exits the cone-shaped portion after bouncing off the reflective surface at location 358, as shown in FIG. 6C. The medium NA light avoids being pushed outside of the system NA transmission window by exiting the lightpipe before bouncing off the reflective surface of the third cone. However, the second cone may not have a substantially zero taper angle in all embodiments of the invention. In one alternative embodiment, the second cone may have a slight negative taper angle so that the original medium NA light is moved towards high NA to further boost the high NA power.

The negative taper angle of the third cone generally functions to convert low NA light into higher NA light. More specifically, the negative taper angle increases the angular distribution of light, which enters the cone-shaped portion with low NA, as well as light converted to low NA within the first cone, by ΔNA. The amount of ΔNA may be generally chosen so that the light redistributed by lightpipe 350 covers an entire NA transmission window of the inspection system. In one embodiment, the amount of ΔNA may be chosen so that the redistributed light covers a NA transmission window of about [0.14, 0.91]. However, one skilled in the art will recognize how the cone-shaped portion could be modified to redistribute the light over substantially any NA transmission window.

As noted above, cone-shaped portion 352 should have a general outer envelop, which transitions smoothly from a zone of increasing cross-sectional area to a zone of decreasing cross-sectional area. The cone-shaped portion may include any number of zones, as long as the outer envelop forms a continuous curve. Three zones (or cones) are described herein having a positive taper angle, a substantially zero taper angle and a negative taper angle. The taper angles may generally be chosen based on the angular distribution of the illumination light and the desired angular distribution of the redistributed light. The lengths of the three zones (or cones) may be chosen, so that the illumination light is prevented from bouncing off the reflective surface of the cone-shaped portion more than twice.

In one embodiment, the first cone may have a length of approximately 17 mm to 21 mm and a positive taper angle of approximately +1° to +2°. The second cone may have a length of approximately 17 mm to 21 mm and a substantially zero taper angle of approximately 0° to +1°. The third cone may have a length of approximately 9 mm to 13 mm and a negative taper angle of approximately −2° to −4°. In one optimization, the positive taper angle may be approximately +1.8°, the substantially zero taper angle may be approximately +10 and the negative taper angle may be approximately −3°. In the same optimization, the length of the first cone may be substantially equal to the length of the second cone. The length of the third cone may be approximately half the length of the first and second cones. However, the actual dimensions of the cone-shape portion 352 may differ from those provided above, depending on the actual angular distribution of the illumination light and the desired angular distribution of the redistributed light. As a rough estimate, the dimensional values provided above for cone length and taper angle may vary by approximately 20%.

After leaving cone-shaped portion 352, the light enters rectangular-shaped portion 354 where it is spatially redistributed across the field stop 390 of the illumination system. Rectangular-shaped portion 354 may be a solid rod through which light rays can travel by total internal reflection. Rectangular-shaped portion 354 is preferably fabricated from the same material (e.g., glass, acrylic, fused silica, plastic or quartz), or at least a material having the same refractive index, as the material used to fabricate the cone-shaped portion 352. Although described as having a rectangular shape, portion 354 may be implemented with other cross-sectional shapes in alternative embodiments of the invention. For instance, portion 354 may alternatively include a rectangular, circular, square or hexagonal cross-sectional shape. The only requirement for the cross sectional shape of the rectangular lightpipe is the size and shape of the system field of view (FOV). If the system FOV is square, a lightpipe with a square cross-sectional shape may be used. If the system FOV is a rectangular, a lightpipe 354 with a rectangular cross-sectional shape may be used, and so forth.

Rectangular-shaped portion 354 differs from cone-shaped portion 352 by having a substantially uniform cross-sectional area along the length of portion 354. In this manner, the rectangular-shaped portion improves the spatial uniformity of the incoming light by randomizing the light as it bounces off the reflective surfaces of the rectangular-shaped portion. Specifically, portion 354 scrambles the spatial distribution of the light, so that the light will be uniformly distributed at the exit of the lightpipe and field stop 390 of the illumination system.

As noted above, rectangular-shaped portion 354 may be bonded to cone-shaped portion 352 in at least one embodiment of the invention. In one embodiment, an optical grade epoxy may be used to bond the exit surface of cone-shaped portion 352 to the entrance surface of rectangular-shaped portion 354. If an epoxy is used, the refractive index of the optical grade epoxy should be substantially equivalent to the refractive index of the material used to fabricate portions 352 and 354. This reduces (or eliminates) unwanted reflections at the interface between the two portions. In another embodiment, a fusion bonding technique may be used to provide optical contact between the cone-shaped and rectangular-shaped portions. A fusion bonding technique may be preferred over the optical grade epoxy in some applications (like DUV applications), where epoxy introduces absorption related damaging issues.

Bonding the two portions of lightpipe 350 together provides many advantages, regardless of the manner in which it is performed. First of all, bonding greatly increases transmission efficiency minimizes light loss through lightpipe 350. Bonding also provides the advantages of reducing system complexity, improving system stability and decreasing alignment errors. As a further advantage, bonding makes the lightpipe easier to make and maintain.

After bonding the two portions together, the total length of lightpipe 350 may be somewhere in the range of about 150 mm. In one embodiment, the length of lightpipe 350 is made substantially equal to 150 mm, so that the lightpipe may be used within existing inspection systems with little to no retrofit concerns. In one embodiment, the lightpipe may be used within one of the BF or DF inspection systems provided by KLA-Tencor of Milpitas, Calif. However, the lightpipe described herein is not limited to having a length of about 150 mm, nor is it limited to use within BF/DF inspection systems or within existing inspection systems. Generally speaking, the total length of the lightpipe may comprise a first length, which is long enough to provide the appropriate amount of angular correction, and a second length, which is long enough to provide the appropriate amount of spatial correction.

After passing through relay optics 360, 380, and 400, the light redistributed by lightpipe 350 passes through beam splitter 410, system pupil 420 and objective lens 430 to illuminate a field of view (FOV) on specimen 440. Objective lens 430 is configured to focus light from the system pupil plane onto the specimen. Objective lens 430 may include any appropriate refractive or reflective lens known in the art. Objective lens 430 may include more than one lens, in some embodiments.

As a result of the redistribution provided by lightpipe 350, the light supplied to specimen 440 will have a uniform angular distribution across system pupil 420 and a uniform spatial distribution across the FOV of the inspection system. However, spatial and angular uniformity is not achieved at the expense of illumination intensity. Instead, lightpipe 350 converts the NA distribution provided by the illumination system into a distribution, which falls within the NA transmission window of the inspection system, with minimum light loss. In some embodiments, lightpipe 350 may provide a light loss of less than about 20%. In a preferred embodiment, lightpipe 350 may provide a light loss of about 10-15%. This represents a significant improvement over conventional lightpipes, which experience large losses (e.g., up to 64% in some cases) by randomly redistributing the light without taking the incident distribution or the final distribution into account.

As shown in FIG. 5, inspection system 300 may also include a detection subsystem. The detection subsystem may include any appropriate detector (or imaging sensor) 460 known in the art, such as a charge coupled device (CCD) or time delay integrating (TDI) camera. The detection subsystem may be generally configured for detecting light propagating from the surface of the specimen 440. The propagating light may be reflected, diffracted and/or scattered from the specimen plane at angles within the imaging NA of the objective lens 430. In one embodiment, the light from specimen 440 is collected by objective lens 430 and reflected to detection lens 450 via beam splitter 410. The beam splitter 410 may comprise a 50/50 beam splitter, for example. In one embodiment, detection lens 450 may comprise any appropriate refractive or reflective lens known in the art. Detection lens 450 may comprise more than one optical element, in some embodiments.

In one embodiment, the position of detection lens 450 may be altered to control the magnification of the light supplied to detector 460. For example, detection lens 450 may be used as a zooming optical element. In one embodiment, the detection lens position may be adjusted, so that the size of the illuminated area on the specimen matches the field of view (FOV) of the imaging sensor 460. In some cases, the detection lens position may be adjusted to minimize the amount of light that falls outside of the FOV of the imaging sensor. In other cases, an aperture stop may be used at the illuminator field stop plane 390 to ensure that the illumination FOV on the specimen 440 is substantially identical to the FOV of the imaging sensor 460.

The focal length of the detection lens can be altered to provide a desired amount of magnification. For example, the magnification of light supplied to the imaging sensor 460 may be determined by the ratio of the focal length of the detection lens 450 to the focal length of the objective lens 430. As noted above, the position and focal length of the objective lens is fixed, so that specimen 440 is located at the front focal plane of the objective lens and system pupil plane 420 is located at the back focal plane of the objective lens. The magnification of light supplied to detector 460 is, therefore, altered by changing the focal length of the detection lens. In one example, the system may be coupled to detection lens 450 so that the system can change the focal length of the detection lens.

The detection subsystem is also configured to generate output signals, which are responsive to light propagating from the specimen. In some embodiments, the output signals generated by the detection subsystem can be used to detect defects on the specimen. For example, the inspection system may also include processor 470. The processor may be coupled to detector 460 by a transmission medium (not shown). The transmission medium may include any suitable transmission medium known in the art. In addition, the processor may be coupled to the detector by one or more electronic components (not shown) such as an analog to digital converter. In this manner, processor 470 may be configured to receive output signals from detector 460.

In some embodiments, processor 470 may be configured to use the output for detecting one or more defects on the specimen. The defects may include any defects of interest on the specimen. In addition, processor 470 may be configured to use the output and any method and/or algorithm known in the art to detect the defects on the specimen. Furthermore, processor 470 may be configured to perform any other inspection-related functions known in the art (e.g., defect location determination, defect classification, defect mapping, etc.). Processor 470 may take various forms, including a personal computer system, mainframe computer system, workstation, image computer, parallel processor, or any other processing device known in the art. In general, the term "computer system" may be broadly defined to encompass any device having one or more processors, which executes instructions from a memory medium.

In some embodiments, the inspection systems described herein may be configured as stand alone tools or tools that are not physically coupled to a process tool. In other embodiments, the inspection systems described herein may be coupled to a process tool (not shown) by a transmission medium, which may include wired and wireless portions. The process tool may include any process tool known in the art such as a lithography tool, an etch tool, a deposition tool, a polishing tool, a plating tool, a cleaning tool, or an ion implantation tool. The process tool may be configured as a cluster tool or a number of process modules coupled by a common handler. Alternatively, the inspection systems described herein may be integrated into a process tool such as those described above.

The results of inspection performed by the systems described herein may be used to alter a parameter of a process or a process tool using a feedback control technique, a feed-forward control technique and/or an in situ control technique. The parameter of the process or the process tool may be altered manually or automatically.

In some embodiments, the illumination system shown in FIG. 5 may be utilized within an existing inspection system. For instance, an existing inspection system may be retrofitted to include an embodiment of the illumination system described herein. The illumination system may replace the existing illumination system used in the inspection system or may be used as an additional illumination system. The illumination system described herein may include an incoherent light source as described further above. As one advantage, using incoherent light to illuminate a specimen substantially eliminates the speckle and ringing, which is often introduced into images when the specimen is illuminated with coherent light (e.g., from a laser source). Eliminating speckle and ringing increases the resolution and sensitivity of the inspection system. In addition, images that do not have artifacts (due to ringing) do not have to be aligned as precisely for image comparison.

Resolution and sensitivity is further increased by redistributing the light generated by the incoherent light source as described herein. As noted above, lightpipe 350 is configured to modify a spatial distribution of the light generated by the incoherent light source, so that the redistributed light is uniformly distributed across a field stop of the illumination system and a FOV of the inspection system. Lightpipe 350 is further configured to modify an angular distribution of the light generated by the incoherent light source, so that the redistributed light is uniformly distributed across a pupil plane of the illumination system and a NA transmission window of the inspection system. Unlike conventional lightpipes, the redistribution of light is performed with minimum light loss and maximum intensity by taking the incident distribution and the final distribution into account. In one embodiment, loss is minimized by designing the lightpipe, so that light is converted from a lower NA distribution to a higher NA distribution without pushing a significant portion of the redistributed light outside of the system transmission NA window.

However, lightpipe 350 is not strictly limited to converting low NA distributions into high NA distributions. In one embodiment, the negative taper angle of the third cone may be modified to convert the predominantly low NA light into substantially any NA region. If the incoming light is predominantly high NA, lightpipe 350 may be modified to convert the high NA light into a lower NA distribution by eliminating the second and third cones and modifying the first cone, as needed. Other modifications may become apparent to one skilled in the art in light of this disclosure.

FIGS. 7-8 illustrate exemplary results of the angular correction provided by the illumination system described herein. More specifically, FIG. 8 illustrates exemplary angular distributions at pupil plane 370 with (■) and without (−) the correction provided by lightpipe 350. As shown in FIG. 7, the angular distribution is more evenly distributed across the pupil plane after correction with lightpipe 350. FIGS. 8A and 8B are simulated pupil plane images at the pupil plane of a bright-field inspection system with (FIG. 8B) and without (FIG. 8A) lightpipe 350. By comparing these images, one skilled in the art would recognize that lightpipe 350 provides uniform spatial and angular distribution, while minimizing brightness reduction (with appropriate choice of lightpipe cross-section that matches the system FOV).

Another embodiment relates to a method 500 for illuminating a specimen. Such a method is illustrated generically in FIG. 9. For example, method 500 may begin 510 by generating incoherent light. In one embodiment, the incoherent light may be generated by a plasma arc lamp and a deep elliptical reflector. As a result, the generated light may have a substantially uneven spatial and angular distribution. Next, the generated light may be directed 520 to a single lightpipe configured to redistribute the angular and spatial distribution of the light in a uniform manner. The single lightpipe may be similar to lightpipe 350. As such, the single lightpipe may comprise a cone-shaped portion configured to redistribute the angular distribution of the light and a rectangular-shaped portion, which is formed contiguous with the cone-shaped portion and configured to redistribute the spatial distribution of light. The redistribution of light may be performed with minimum light loss. Finally, the redistributed light may be transmitted 530 onto a specimen for illuminating a field of view on the specimen. The redistributed light may be uniformly spatially distributed across the entire field of view on the specimen, as well as uniformly angularly distributed across the entire NA transmission window of a system configured for inspecting the specimen.

It will be appreciated to those skilled in the art having the benefit of this disclosure that this invention is believed to provide improved systems and methods for illuminating a specimen. More specifically, the invention provides an improved lightpipe configured for modifying the spatial and the angular distribution of light generated by an incoherent light source. Further modifications and alternative embodiments of various aspects of the invention will be apparent to those skilled in the art in view of this description. It is intended, therefore, that the following claims be interpreted to embrace all such modifications and changes and, accordingly, the specification and drawings are to be regarded in an illustrative rather than a restrictive sense.

What is claimed is:

1. A system configured to illuminate a specimen, the system comprising:
   an illumination source configured to generate light with an uneven distribution at an illumination plane of the system;
   a lightpipe coupled for redistributing the light, wherein the lightpipe comprises; (i) a cone-shaped portion including a first cone, whose cross-sectional area increases along a length of the first cone, and a second cone whose cross-sectional area decreases along a length of the second cone, and (ii) a rectangular-shaped portion formed continuous with the second cone; and
   at least one optical element configured to direct the redistributed light onto the specimen.

2. The system as recited in claim 1, wherein the illumination source comprises a plasma arc lamp including a plasma source and a elliptical reflector.

3. The system as recited in claim 2, wherein the plasma source is selected from a group consisting of Mercury (Hg) and Mercury Xenon (HgXe) sources.

4. The system as recited in claim 2, wherein the elliptical reflector includes a relatively deep ellipse with an eccentricity close to 1.

5. The system as recited in claim 1, wherein the cone-shaped portion is configured for modifying an angular distribution of the generated light, so that the redistributed light is uniformly distributed across a pupil plane of the system.

6. The system as recited in claim 1, wherein the rectangular-shaped portion is configured for modifying a spatial distribution of the generated light, so that the redistributed light is uniformly distributed across a field stop of the system.

7. The system as recited in claim 1, wherein the rectangular and cone-shaped portions are fabricated separately and bonded together at opposing ends, wherein said bonding creates an optically seamless transition between the rectangular and cone-shaped portions.

8. The system as recited in claim 1, wherein the first cone is formed contiguous with the second cone.

9. The system as recited in claim 1, wherein the cone-shaped portion includes a third cone formed between and contiguous with the first and second cone.

10. The system as recited in claim 9, wherein the third cone comprises a relatively uniform cross-section along an entire length of the third cone.

11. The system as recited in claim 9, wherein the cross-sectional area of the third cone decreases along a length of the third cone.

12. The system as recited in claim 9, wherein the length of the first cone is approximately equal to the length of the third cone, and wherein the length of the second cone is approximately half the length of the first and third cones.

13. The system as recited in claim 9, wherein the first cone comprises a positive taper angle, wherein the third cone comprises a substantially zero taper angle, and wherein the second cone comprises a negative taper angle.

14. The system as recited in claim 13, wherein:
the positive taper angle is adapted to convert an angular distribution of the generated light, which enters the cone-shaped portion at high angles, into lower angles;
the substantially zero taper angle is adapted to preserve an angular distribution of the generated light, which enters the cone-shaped portion at medium angles; and
the negative taper angle is adapted to convert an angular distribution of the generated light, which enters the cone-shaped portion at low angles, as well as light converted to low angles by the positive taper angle, into higher angles.

15. A system for inspecting a specimen, the system comprising:
an illumination source comprising a plasma source and an elliptical reflector;
a lightpipe coupled for receiving an uneven distribution of light from the illumination source, wherein the lightpipe comprises a cone-shaped portion formed contiguous with a rectangular-shaped portion;
at least one optical element configured to direct light, which has been redistributed by the lightpipe, onto a surface of the specimen; and
a detection subsystem configured to generate output signals in response to light propagating from the surface of the specimen, and wherein the output signals are used to inspect the specimen.

16. The system as recited in claim 15, wherein a total length of the lightpipe is about 150 mm.

17. The system as recited in claim 15, wherein the rectangular-shaped portion is configured for modifying a spatial distribution of the light generated by the illumination source, so that the redistributed light is uniformly distributed across a field stop of the system.

18. The system as recited in claim 15, wherein the cone-shaped portion is configured for modifying an angular distribution of the light generated by the illumination source, so that the redistributed light is uniformly distributed across a pupil plane of the system.

19. The system as recited in claim 18, wherein the light generated by the illumination source enters the cone-shaped portion with low, medium and high numerical apertures (NA), and wherein the cone-shaped portion comprises:
a first cone having a positive taper angle for converting light that enters the cone-shaped portion with high NA into lower NA;
a second cone having a substantially zero taper angle for preserving light that enters the cone-shaped portion with medium NA; and
a third cone having a negative taper angle for increasing the numerical aperture of substantially all light that enters the cone-shaped portion by $\Delta NA$.

20. The system as recited in claim 19, wherein the cone-shaped portion is configured to redistribute the light evenly over an entire system transmission numerical aperture (NA) window without significant light loss.

21. The system as recited in claim 19, wherein the lightpipe provides a light loss of less than about 20%.

22. The system as recited in claim 19, wherein the lightpipe provides a light loss of about 10-15%.

* * * * *

UNITED STATES PATENT AND TRADEMARK OFFICE
CERTIFICATE OF CORRECTION

| | | |
|---|---|---|
| PATENT NO. | : 7,654,715 B1 | Page 1 of 1 |
| APPLICATION NO. | : 11/836216 | |
| DATED | : February 2, 2010 | |
| INVENTOR(S) | : Chen et al. | |

It is certified that error appears in the above-identified patent and that said Letters Patent is hereby corrected as shown below:

Col. 18, line 57, after "comprises" please delete ";" and substitute --:--.

Col. 18, lines 61-62, after "formed" please delete "continuous" and substitute --contiguous--.

Signed and Sealed this

Eighteenth Day of May, 2010

David J. Kappos
*Director of the United States Patent and Trademark Office*